(12) United States Patent
Kimmerling

(10) Patent No.: US 10,780,169 B2
(45) Date of Patent: Sep. 22, 2020

(54) METHOD OF DECREASING DERMAL ABSORPTION USING COMPOSITION COMPRISING SILOXANE POLYMER

(71) Applicant: Kimmerling Holdings Group LLC, Marietta, GA (US)

(72) Inventor: Kirk A. Kimmerling, Kennesaw, GA (US)

(73) Assignee: Kimmerling Holdings Group, LLC, Marietta, GA (US)

( * ) Notice: Subject to any disclaimer, the term of this patent is extended or adjusted under 35 U.S.C. 154(b) by 0 days.

(21) Appl. No.: 16/838,717

(22) Filed: Apr. 2, 2020

(65) Prior Publication Data

US 2020/0230243 A1 Jul. 23, 2020

Related U.S. Application Data

(63) Continuation of application No. 16/132,909, filed on Sep. 17, 2018, which is a continuation of application No. PCT/US2017/054228, filed on Sep. 29, 2017.

(60) Provisional application No. 62/409,091, filed on Oct. 17, 2016.

(51) Int. Cl.

| | |
|---|---|
| *A61Q 19/00* | (2006.01) |
| *A61K 47/34* | (2017.01) |
| *A61K 31/14* | (2006.01) |
| *A61K 33/38* | (2006.01) |
| *A61K 33/30* | (2006.01) |
| *A61Q 17/00* | (2006.01) |
| *A61K 47/14* | (2017.01) |
| *A61K 8/58* | (2006.01) |
| *A61K 8/37* | (2006.01) |
| *A61K 31/695* | (2006.01) |
| *A61K 8/891* | (2006.01) |
| *A61K 47/24* | (2006.01) |

(52) U.S. Cl.
CPC ............ *A61K 47/34* (2013.01); *A61K 8/375* (2013.01); *A61K 8/585* (2013.01); *A61K 8/891* (2013.01); *A61K 31/14* (2013.01); *A61K 31/695* (2013.01); *A61K 33/30* (2013.01); *A61K 33/38* (2013.01); *A61K 47/14* (2013.01); *A61K 47/24* (2013.01); *A61Q 17/005* (2013.01); *A61Q 19/00* (2013.01)

(58) Field of Classification Search
None
See application file for complete search history.

(56) References Cited

U.S. PATENT DOCUMENTS

| | | |
|---|---|---|
| 5,725,875 A | 3/1998 | Noll et al. |
| 6,187,327 B1 | 2/2001 | Stack |
| 2010/0080768 A1 | 4/2010 | McGraw et al. |
| 2013/0230676 A1 | 9/2013 | Blizzard et al. |
| 2014/0086857 A1 | 3/2014 | Blizzard |
| 2015/0328241 A1 | 11/2015 | Hilliard et al. |

FOREIGN PATENT DOCUMENTS

| | | |
|---|---|---|
| WO | 2016057630 | 4/2016 |

OTHER PUBLICATIONS

International Search Report and Written Opinion issued in corresponding application No. PCT/US2017/054228, dated Dec. 15, 2017, 10 pgs.
Extended European Search Report issued for Application No. 17862811, dated May 14, 2020.

*Primary Examiner* — Jyothsna A Venkat
(74) *Attorney, Agent, or Firm* — Meunier Carlin & Curfman LLC

(57) ABSTRACT

Methods of reducing dermal penetration of at least one active ingredient in a topically applied product using compositions comprising siloxane polymers are disclosed. In some aspects, the active ingredient is an antimicrobial agent, especially benzalkonium chloride, 3-(trimethoxysilyl) propyldimethyloctadecyl ammonium chloride, and combinations thereof.

2 Claims, No Drawings

METHOD OF DECREASING DERMAL ABSORPTION USING COMPOSITION COMPRISING SILOXANE POLYMER

CROSS REFERENCE TO RELATED APPLICATIONS

This application is a continuation of U.S. application Ser. No. 16/132,909, filed Sep. 17, 2018, which is a continuation of PCT/US2017/054228, filed Sep. 29, 2017, and claims the benefit of priority to U.S. Provisional Application No. 62/409,091, filed Oct. 17, 2016, both each of where are incorporated herein by reference.

FIELD OF THE INVENTION

The invention relates to methods of decreasing dermal absorption of an active ingredient, such as an antimicrobial, using composition comprising siloxane polymer.

BACKGROUND OF THE INVENTION

Frequent reapplication of alcohol-based hand sanitizers by users, such as by hospital workers and medical and dental staff, may lead to elevated blood alcohol content. Thus, it would be useful to provide a base for hand sanitizers and for any application of an active ingredient to the skin, nails, hair, or lips that would prevent the penetration of the active ingredient through the skin, nails, hair, or lips into the body to prevent toxicity. It would also be useful to provide a base for hand sanitizers that promotes substantivity, even after repeated applications, washings, donning/doffing of gloves, and use of the hands. The invention is directed to these, as well as other, important ends.

SUMMARY OF THE INVENTION

Accordingly, in one aspect, the invention is directed to methods of reducing dermal penetration of at least one active ingredient in a topically applied product, comprising:
 providing a composition, comprising:
 A. a siloxane gel comprising:
 1. a first solvent selected from the group consisting of:
  a. organic compounds;
  b. compounds containing a silicon atom;
  c. mixtures of organic compounds;
  d. mixtures of compounds containing a silicon atom; and
  e. mixtures of organic compounds and compounds containing a silicon atom;
 2. a siloxane copolymer comprising a reaction product of:
  a. an hydridopolysiloxane selected from the group consisting of:
   i. $R_3SiO(R'_2SiO)_a(R''HSiO)_bSiR_3$;
   ii. $HR_2SiO(R'_2SiO)_cSiR_2H$; and
   iii $HR_2SiO(R'_2SiO)_a(R''HSiO)_bSiR_2H$;
  wherein:
   R, R', R" are, each independently, $C_1$-$C_6$ alkyl;
   a is about 0 to about 250;
   b is about 1 to about 250; and
   c is about 0 to about 250; and
  b. an α,ω-diene having the general formula:

$CH_2=CH(CH_2)_xCH=CH_2$ wherein:
   x is about 1 to about 20;

B. a first additional solvent selected from the group consisting of:
  1. organic compounds;
  2. compounds containing a silicon atom;
  3. mixtures of organic compounds;
  4. mixtures of compounds containing a silicon atom; and
  5. mixtures of organic compounds and compounds containing a silicon atom;
 C. a second additional solvent selected from the group consisting of
  1. organic compounds,
  2. compounds containing a silicon atom;
  3. mixtures of organic compounds;
  4. mixtures of compounds containing a silicon atom; and
  5. mixtures of organic compounds and compounds containing a silicon atom;
 D. said at least active ingredient;
 topically applying said composition to the skin of a user;
 drying said topically applied composition;
 topically reapplying said composition to the skin of said user at least one time, and
 drying said topically reapplied composition.

DETAILED DESCRIPTION OF THE INVENTION

The present invention may be understood more readily by reference to the following detailed description of the invention and the Examples included therein.

As employed above and throughout the disclosure, the following terms, unless otherwise indicated, shall be understood to have the following meanings.

As used herein, the singular forms "a," "an," and "the" include the plural reference unless the context clearly indicates otherwise.

"Alkyl," as used herein, refers to an optionally-substituted, saturated straight, branched, or cyclic hydrocarbon having from about 1 to about 20 carbon atoms (and all combinations and subcombinations of ranges and specific numbers of carbon atoms therein), with from about 1 to about 8 carbon atoms or 1 to 6 carbon atoms ($C_1$-$C_6$) being preferred, and with from about 1 to about 4 carbon atoms. Alkyl groups include, but are not limited to, methyl, ethyl, n-propyl, isopropyl, n-butyl, isobutyl, t-butyl, n-pentyl, cyclopentyl, cyclopropyl, isopentyl, neopentyl, n-hexyl, isohexyl, cyclohexyl, cyclooctyl, adamantyl, 3-methylpentyl, 2,2-dimethylbutyl, and 2,3-dimethylbutyl. A branched alkyl group has at least 3 carbon atoms (e.g., an isopropyl group), and in various aspects, has up to 6 carbon atoms, i.e., a branched lower alkyl group. A branched alkyl group has at least 3 carbon atoms (e.g., an isopropyl group), and in various aspects, has up to 6 carbon atoms, i.e., a branched lower alkyl group.

"Alkenyl," as used herein, refers to an optionally-substituted, singly unsaturated, straight, branched, or cyclic hydrocarbon having from about 2 to about 20 carbon atoms (and all combinations and subcombinations of ranges and specific numbers of carbon atoms therein), with from about 2 to about 8 carbon atoms or 2 to 6 carbon atoms ($C_2$-$C_6$) being preferred. Alkenyl groups include, but are not limited to, ethenyl (or vinyl), allyl, propenyl, butenyl, pentenyl, cyclopentenyl, hexenyl, and octenyl.

"Alkylenyl," as used herein, refer to the subsets of alkyl groups, as defined herein, including the same residues as alkyl but having two points of attachment within a chemical structure. Examples of ($C_1$-$C_6$)alkylenyl include methylenyl (—CH$_2$—), ethylenyl (—CH$_2$CH$_2$—), propylenyl (—CH$_2$CH$_2$CH$_2$—), and dimethylpropylenyl (—CH$_2$C(CH$_3$)$_2$CH$_2$—).

"Aryl," as used herein, refers to an optionally-substituted, mono-, di-, tri-, or other multicyclic aromatic ring system having from about 5 to about 50 carbon atoms (and all combinations and subcombinations of ranges and specific numbers of carbon atoms therein), with from about 6 to about 10 carbons (C$_6$-C$_{10}$) being preferred. Non-limiting examples include, for example, phenyl, naphthyl, anthracenyl, and phenanthrenyl.

As used herein, the terms "optionally-substituted" or "substituted" are intended to refer to the optional replacement of up to four hydrogen atoms with up to four independently selected substituent groups as defined herein. Unless otherwise specified, suitable substituent groups independently include hydroxyl, nitro, amino, imino, cyano, halo, thio, sulfonyl, aminocarbonyl, carbonylamino, carbonyl, oxo, guanidine, carboxyl, formyl, alkyl, perfluoroalkyl, alkylamino, dialkylamino, alkoxy, alkoxyalkyl, alkylcarbonyl, arylcarbonyl, alkylthio, aryl, heteroaryl, a heterocyclic ring, cycloalkyl, hydroxyalkyl, carboxyalkyl, haloalkyl, alkenyl, alkynyl, arylalkyl, aryloxy, heteroaryloxy, heteroarylalkyl, and the like. Substituent groups that have one or more available hydrogen atoms can in turn optionally bear further independently selected substituents, to a maximum of three levels of substitutions. For example, the term "optionally-substituted alkyl" is intended to mean an alkyl group that can optionally have up to four of its hydrogen atoms replaced with substituent groups as defined above (i.e., a first level of substitution), wherein each of the substituent groups attached to the alkyl group can optionally have up to four of its hydrogen atoms replaced by substituent groups as defined above (i.e., a second level of substitution), and each of the substituent groups of the second level of substitution can optionally have up to four of its hydrogen atoms replaced by substituent groups as defined above (i.e., a third level of substitution).

While the present invention is capable of being embodied in various forms, the description below of several aspects is made with the understanding that the present disclosure is to be considered as an exemplification of the invention, and is not intended to limit the invention to the specific aspects illustrated. Headings are provided for convenience only and are not to be construed to limit the invention in any manner. Aspects illustrated under any heading may be combined with aspects illustrated under any other heading.

The use of numerical values in the various quantitative values specified in this application, unless expressly indicated otherwise, are stated as approximations as though the minimum and maximum values within the stated ranges were both preceded by the word "about." In this manner, slight variations from a stated value can be used to achieve substantially the same results as the stated value. Also, the disclosure of ranges is intended as a continuous range including every value between the minimum and maximum values recited as well as any ranges that can be formed by such values. Also disclosed herein are any and all ratios (and ranges of any such ratios) that can be formed by dividing a recited numeric value into any other recited numeric value. Accordingly, the skilled person will appreciate that many such ratios, ranges, and ranges of ratios can be unambiguously derived from the numerical values presented herein and in all instances such ratios, ranges, and ranges of ratios represent various aspects of the present invention.

As used herein, the phrase "substantially" means have no more than about 10% difference between the target and actual level, preferably less than about 5% difference, more preferably, less than about 1% difference.

As used herein, the term "user" can be a vertebrate, such as a mammal, a fish, a bird, a reptile, or an amphibian. Thus, the subject of the herein disclosed methods can be a human, non-human primate, horse, pig, rabbit, dog, sheep, goat, cow, cat, guinea pig or rodent. The term does not denote a particular age or sex. Thus, adult and newborn subjects, as well as fetuses, whether male or female, are intended to be covered. In one aspect, the user is a mammal. The term "user" includes human and veterinary subjects.

While the present invention is capable of being embodied in various forms, the description below of several aspects is made with the understanding that the present disclosure is to be considered as an exemplification of the invention, and is not intended to limit the invention to the specific aspects illustrated. Headings are provided for convenience only and are not to be construed to limit the invention in any manner. Aspects illustrated under any heading may be combined with aspects illustrated under any other heading.

The use of numerical values in the various quantitative values specified in this application, unless expressly indicated otherwise, are stated as approximations as though the minimum and maximum values within the stated ranges were both preceded by the word "about." In this manner, slight variations from a stated value can be used to achieve substantially the same results as the stated value. Also, the disclosure of ranges is intended as a continuous range including every value between the minimum and maximum values recited as well as any ranges that can be formed by such values. Also disclosed herein are any and all ratios (and ranges of any such ratios) that can be formed by dividing a recited numeric value into any other recited numeric value. Accordingly, the skilled person will appreciate that many such ratios, ranges, and ranges of ratios can be unambiguously derived from the numerical values presented herein and in all instances such ratios, ranges, and ranges of ratios represent various aspects of the present invention.

Accordingly, in one aspect, the invention is directed to methods of reducing dermal penetration of at least one active ingredient in a topically applied product, comprising:
providing a composition, comprising:
A. a siloxane gel comprising:
  1. a first solvent selected from the group consisting of:
    a. organic compounds;
    b. compounds containing a silicon atom;
    c. mixtures of organic compounds;
    d. mixtures of compounds containing a silicon atom; and
    e. mixtures of organic compounds and compounds containing a silicon atom;
  2. a siloxane copolymer comprising a reaction product of:
    a. an hydridopolysiloxane selected from the group consisting of:
      i. R$_3$SiO(R'$_2$SiO)$_a$(R"HSiO)$_b$SiR$_3$;
      ii. HR$_2$SiO(R'$_2$SiO)$_c$SiR$_2$H; and
      iii HR$_2$SiO(R'$_2$SiO)$_a$(R"HSiO)$_b$SiR$_2$H;
    wherein:
      R, R', R" are, each independently, C$_1$-C$_6$alkyl;
      a is about 0 to about 250;
      b is about 1 to about 250; and
      c is about 0 to about 250; and b. an α,ω-diene having the general formula:

$$CH_2=CH(CH_2)_xCH=CH_2$$

wherein:
x is about 1 to about 20;
B. a first additional solvent selected from the group consisting of:
1. organic compounds;
2. compounds containing a silicon atom;
3. mixtures of organic compounds;
4. mixtures of compounds containing a silicon atom; and
5. mixtures of organic compounds and compounds containing a silicon atom;
C. a second additional solvent selected from the group consisting of:
1. organic compounds;
2. compounds containing a silicon atom;
3. mixtures of organic compounds,
4. mixtures of compounds containing a silicon atom; and
5. mixtures of organic compounds and compounds containing a silicon atom;
D. said at least active ingredient;
topically applying said composition to the skin (which, as used herein, includes skin, hair, nails, and lips) of a user;
drying (wherein the drying may be active or passive (air drying)) said topically applied composition;
topically reapplying said composition to the skin of said user at least one time; and
drying said topically reapplied composition.

In certain aspects of the method, the active ingredient is an agent selected from the group consisting of:
pesticides, such as fungicides, herbicides, insecticides, algicides, molluscides, miticides, rodenticides, and the like;
antimicrobials, such as germicides, antibiotics, antibacterials, antivirals, antifungals, antiprotozoals, antiparasitics, and the like;
spermicides;
insect repellents;
uv absorbers;
iodine;
bromine;
chlorine;
titanium dioxide;
zinc oxide;
silver and silver compounds;
copper and copper compounds; and
mixtures thereof.

Suitable antimicrobials include, but are not limited to, quaternary ammonium compounds, such as benzalkonium chloride ($C_6H_5CH_2N(CH_3)_2RCl$ where R is ($C_1$-$C_{20}$) alkyl, benzethonium chloride, and other ammonium chlorides (including dodecyl dimethyl ammonium chloride, dodecyl trimethyl ammonium chlorine, dodecyl benzyldimethyl ammonium chlorides, and the like);
hexachlorophene;
chloroxylenol;
biguanides, bis-biguanides, and polybiguanides (such as chlorhexidine, polyaminopropyl biguanide (PAPB), polyhexamethylene biguanide (PHMB), and the like);
antimicrobial peptides and nucleotides;
silicon-containing antimicrobial agent;
antimicrobial metals and metal salts (such as silver and silver salts (including silver nitrate and silver sulfadiazine (SSD)) and copper and copper salts);
an alcohol selected from the group consisting of methanol, ethanol, n-propanol, isopropanol, and mixtures thereof; and
mixtures thereof.

In certain aspects of the method, the silicon-containing antimicrobial agent is a compound of formula I:

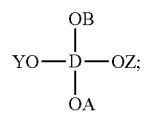

wherein:
D is independently Si, Ti, Al, or Zr;
A, B, Y, and Z are each independently selected from the group consisting of H, ($C_1$-$C_8$)alkyl, trifluoro-substituted ($C_1$-$C_5$)alkyl, and

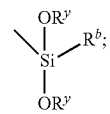

$R^b$ is independently

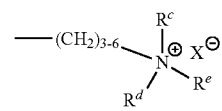

wherein:
R is ($C_1$-$C_2$)alkyl;
$R^d$ is ($C_1$-$C_2$)alkyl or phenyl;
Re is ($C_6$-$C_{22}$)alkyl;
X' is an anion selected from the group consisting of chloride, bromide, fluoride, iodide, sulfonate, and acetate;
each $R^y$ is, independently, H, ($C_1$-$C_8$)alkyl, or trifluoro-substituted ($C_1$-$C_8$)alkyl; and
wherein at least one of A, B, Y, and Z is

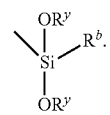

In certain aspects of the method, the active ingredient is selected from the group consisting of:
benzalkonium chloride;
silicon-containing antimicrobial agent is a compound of formula:

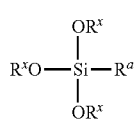

wherein:

R$^x$ is H or C$_1$-C$_4$alkyl; and

R$^a$ is —(C$_3$-C$_6$)alkylenyl-dimethyl-(C$_6$-C$_{22}$alkyl) quaternary ammonium chloride or —(C$_3$-C$_6$)alkylenyl-methyl-phenyl-(C$_6$-C$_{22}$alkyl) quaternary ammonium chloride; and combinations thereof.

In certain aspects of the method, the active ingredient is selected from the group consisting of:

benzalkonium chloride;

silicon-containing antimicrobial agent selected from the group consisting of:

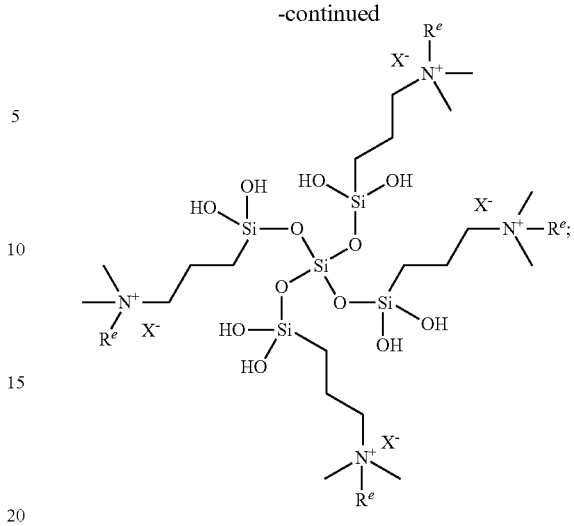

and mixtures thereof; and combinations thereof.

In certain aspects of the method, the active ingredient is selected from the group consisting of:

benzalkonium chloride;

3-(trimethoxysilyl) propyldimethyloctadecyl ammonium chloride; and combinations thereof.

In certain aspects of the method, the active ingredient is benzalkonium chloride.

In certain aspects of the method, the active ingredient is 3-(trimethoxysilyl) propyldimethyloctadecyl ammonium chloride.

In certain aspects of the method, the active ingredient is a combination of benzalkonium chloride and 3-(trimethoxysilyl) propyldimethyloctadecyl ammonium chloride.

In certain aspects of the method, the active ingredient comprises:

about 0.01% to about 0.5%, by weight, based on the total weight of the composition, of benzalkonium chloride; and about 0.1% to about 20%, by weight, based on the total weight of the composition, of 3-(trimethoxysilyl) propyldimethyloctadecyl ammonium chloride.

In certain aspects of the method, the antimicrobial agent is a metal salt.

In certain aspects of the method, the siloxane copolymer is dimethicone crosspolymer.

In certain aspects of the method, the first solvent is selected from the group consisting of: methylsiloxane cyclics having 4 and 5 silicon atoms, a trimethylsiloxy end-blocked polydimethylsiloxane, ester of aromatic alkoxylated alcohol and fatty carboxylic acid, alkoxylated derivatives of benzyl alcohol, and mixtures thereof.

In certain aspects of the method, the first additional solvent is selected from the group consisting of: methylsiloxane cyclics having 4 and 5 silicon atoms, a trimethylsiloxy end-blocked polydimethylsiloxane, ester of aromatic alkoxylated alcohol and fatty carboxylic acid, alkoxylated derivatives of benzyl alcohol, and mixtures thereof.

In certain aspects of the method, the second additional solvent is selected from the group consisting of: methylsiloxane cyclics having 4 and 5 silicon atoms, a trimethylsiloxy end-blocked polydimethylsiloxane, ester of aromatic alkoxylated alcohol and fatty carboxylic acid, alkoxylated derivatives of benzyl alcohol, and mixtures thereof.

In certain aspects of the method, the siloxane copolymer is dimethicone crosspolymer.

In certain aspects of the method, the composition, comprises:
dimethicone crosspolymer; cyclopentasiloxane;
PPG-3 benzyl ether ethyl hexanoate;
octadecyldimethyl trimethoxysilylpropyl ammonium chloride; and
benzalkonium chloride.

In certain aspects of the method, the composition is reapplied at least three times in a one hour period. In certain aspects of the method, the composition is reapplied at least three times in a four hour period. In certain aspects of the method, the composition is reapplied at least seven times in an eight hour period. In certain aspects of the method, the composition is reapplied at least 100 times in a twelve hour period.

In certain aspects of the method, the user washes said skin with an aqueous-based cleanser:
before said applying step;
before any one said reapplying steps; or
any combination of steps thereof.

In other aspect of the method, it has been found that despite multiple washings, donning and doffing of gloves or other protective equipment, and/or daily activity (such as patient care and cleaning), and apparent removal of the vehicle for the active ingredient(s), the compositions useful in the methods show substantivity (i.e., the ability of the topically-applied compositions to adhere and retain their properties, especially those of the active ingredient(s), after the skin is exposed to water (sweating, swimming, bathing, and/or friction, among other factors). This substantivity is seen with the multiple reapplying steps.

The compositions useful in the methods described herein may be prepared in the following manner.

preparing a siloxane polymer thixotropic base, comprising:
reacting to form a copolymer:
i. a ≡Si—H containing polysiloxane selected from the group consisting of:
(a) $R_3SiO(R'_2SiO)_a(R''HSiO)_bSiR_3$;
(b) $HR_2SiO(R'_2SiO)_cSiR_2H$; and
(c) $HR_2SiO(R'_2SiO)_a(R''HSiO)_bSiR_2H$;
wherein;
R, R', R" are, each independently, $C_1$-$C_6$alkyl;
a is about 0 to about 250;
b is about 1 to about 250; and
c is about 0 to about 250; and
ii. an α,ω-diene having the general formula:

wherein:
x is about 1 to about 20;
wherein said reaction is carried out in the presence of a Noble metal catalyst and a first solvent selected from the group consisting of:
i. organic compounds;
ii. compounds containing a silicon atom;
iii. mixtures of organic compounds;
iv. mixtures of compounds containing a silicon atom; and
v. mixtures of organic compounds and compounds containing a silicon atom; and
wherein said reaction is continued until a gel is formed by crosslinking and addition of said ≡Si—H across double bonds in said alpha, omega-diene;

adding a first additional solvent to said gel and subjecting said first additional solvent and said gel to shear force until a siloxane paste is formed;
wherein said first additional solvent selected from the group consisting of:
i. organic compounds;
ii. compounds containing a silicon atom;
iii. mixtures of organic compounds;
iv. mixtures of compounds containing a silicon atom, and
v. mixtures of organic compounds and compounds containing a silicon atom;
adding a second additional solvent to said siloxane paste and blending said second additional solvent and said siloxane paste by mixing until said siloxane polymer thixotropic base is formed;
wherein said second additional solvent selected from the group consisting of
i. organic compounds,
ii. compounds containing a silicon atom;
iii. mixtures of organic compounds;
iv. mixtures of compounds containing a silicon atom; and
v. mixtures of organic compounds and compounds containing a silicon atom.

The active ingredient(s) may be added to the composition at the requisite level(s) and mixed to incorporate the active ingredient(s) into the composition.

In certain aspects, the method further comprises:
adding to said siloxane gel, said siloxane paste, or said siloxane polymer thixotropic base at least one component selected from the group consisting of: medicament, antibiotic, analgesic, essential oil, preservative, colorant, fragrance, and mixtures thereof.

Carrying out of the process is simply a matter of combining the ≡Si—H containing polysiloxane, the alpha, omega-diene, the low molecular weight silicone oil or other solvent, and the catalyst; mixing these ingredients at room temperature until a gel is formed. Higher temperatures to speed up the process can be used, if desired.

First additional amounts of the low molecular weight silicone oil or solvent are then added to the gel, and the resulting mixture is subjected to shear force to form the paste.

Any type of mixing and shearing equipment may be used to perform these steps such as a batch mixer, planetary mixer, single or multiple screw extruder, dynamic or static mixer, colloid mill, homogenizer, sonolator, or a combination thereof. The low molecular weight silicone oil or other solvent is present at levels generally within the range of about 65% by weight to about 98% by weight, based on the total weight of the composition, preferably about 80% by weight to about 98% by weight, based on the total weight of the composition.

To prepare the siloxane polymer thixotropic base, a second addition of a solvent is added to the paste described just supra.

The solvents useful for this addition include organic compounds, compounds containing a silicon atom, mixtures of organic compounds, mixtures of compounds containing a silicon atom, or mixtures of organic compounds and compounds containing a silicon atom, used on an industrial scale to dissolve, suspend, or change the physical properties of other materials. There is minimal or no phase separation, especially with the aromatic oils.

Preferred for the second solvent are low molecular weight silicone oils, and as set forth supra, it is intended herein to include low molecular weight linear and cyclic volatile methyl siloxanes, low molecular weight linear and cyclic volatile and non-volatile alkyl and aryl siloxanes, and low molecular weight linear and cyclic functional siloxanes.

Also preferred for the second solvent are organic compounds such as, for example, esters of aromatic alkoxylated alcohols and fatty carboxylic acids having the general formula R'O-[Alk-O]—R", wherein R' is an organic moiety that contains at least one aromatic nucleus RN; R" is a fatty alkyl group; and -[Alk-O]- is an alkoxy spacer, preferably $C_1$-$C_{20}$alkyoxy spacer.

The aromatic nucleus RN may contain from 6 to 20 carbon atoms exclusive of substitution. Nuclei RN having 6 to 10 carbon atoms are preferred. Non-limiting examples of the aromatic nuclei RN are benzene, naphthalene and anthracene nuclei, which contain 6, 10, and 14 carbon atoms, respectively. The preferred method for combining the second solvent into the paste is simple blending rather than shear mixing.

The siloxane polymer thixotropic base has been found useful as a carrier or vehicle for a multitude of active ingredients that are beneficial as cosmetics; pharmaceuticals; antimicrobial, antifungal, antialgae agents; medicaments; bug repellents, coagulants or hemostatic agent, and the like.

Some representative examples of suitable α,ω-diene for use herein are 1,4-pentadiene; 1,5-hexadiene; 1,6-heptadiene; 1,7-octadiene; 1,8-nonadiene; 1,9-decadiene; 1,11-dodecadiene; 1,13-tetradecadiene; and 1,19-eicosadiene.

The addition and crosslinking reaction requires a catalyst to effect the reaction between the ≡SiH containing polysiloxane and the α,ω-diene. Suitable catalysts are Group VIII transition metals, i.e., the Noble metals. Such Noble metal catalysts are described in U.S. Pat. No. 3,923,705, incorporated herein by reference, to show platinum catalysts. One preferred platinum catalyst is Karstedt's catalyst, which is described in U.S. Pat. Nos. 3,715,334 and 3,814,730, incorporated herein by reference. Karstedt's catalyst is a platinum divinyl tetramethyl disiloxane complex typically containing about one weight percent of platinum in a solvent such as toluene. Another preferred platinum catalyst is a reaction product of chloroplatinic acid and an organosilicon compound containing terminal aliphatic unsaturation. It is described in U.S. Pat. No. 3,419,593, incorporated herein by reference. The Noble metal catalysts are used in amounts from about 0.00001 to about 0.5 parts per 110 weight parts of the ≡SiH containing polysiloxane, preferable about 0.00001 to about 0.02 parts, most preferable is about 0.0001 to about 0.002 parts.

The ≡Si—H containing polysiloxane are commercially available and are described hereinafter.

The phrase "low molecular weight silicone oil" is intended herein to include low molecular weight linear and cyclic volatile methyl siloxanes, low molecular weight linear and cyclic volatile and non-volatile alkyl and aryl siloxanes, and low molecular weight linear and cyclic functional siloxanes. Most preferred, however, are low molecular weight linear and cyclic volatile methyl siloxanes (VMS).

Volatile methyl siloxanes correspond to the average unit formula $(CH_3)_aSiO_{(4-a)/2}$ in which a has an average value of two to three. The compounds contain siloxane units joined by Si—O—Si bonds. Representative units are monofunctional "M" units $(CH_3)_3SiO_{1/2}$ and difunctional "D" units $(CH_3)_3SiO_{2/2}$.

The presence of trifunctional "T" units $CH_3SiO_{3/2}$ results in the formation of branched linear or cyclic volatile methylsiloxanes. The presence of tetrafunctional "Q" units $SiO_{4/2}$ units results in the formation of branched linear or cyclic volatile methyl siloxanes.

Linear volatile methyl siloxanes have the formula $(CH_3)_3SiO\{(CH_3)_2SiO\}_ySi(CH_3)_3$. The value of y is 0 to 5. Cyclic volatile methyl siloxanes have the formula $\{(CH_3)_2SiO\}_x$. The value of z is 3 to 6. Preferable, these volatile methyl siloxanes have boiling points less than about 250° C. and viscosities of about 0.65 to 5.0 centistokes (mm²/s).

Representative linear polysiloxanes are compounds of the formula $R_3SiO(R_2SiO)_ySiR_3$, and representative cyclic polysiloxanes are compounds of the formula $(R_2SiO)_z$. R is an alkyl group of 1 to 6 carbon atoms, or an aryl group such as phenyl. The value of y is 0 to 80, preferably 0 to 20. The value of z is 0 to 9, preferably 4 to 6. These polysiloxanes have viscosities generally in the range of about 1 to 100 centistokes (mm²/s).

The invention herein is not limited to swelling silicone elastomers with only low molecular weight polysiloxanes. Other types of solvents can swell the silicone elastomer. Thus, a single solvent or a mixture of solvents may be used.

By "solvent" we mean organic compounds, compounds containing a silicon atom, mixtures of organic compounds, mixtures of compounds containing a silicon atom, or mixtures of organic compounds and compounds containing a silicon atom, used on an industrial scale to dissolve, suspend, or change the physical properties of other materials.

In general, the organic compounds are aromatic hydrocarbons, aliphatic hydrocarbons, alcohols, aldehydes, ketones, amines, esters, ethers, glycols, glycol ethers, alkyl halides, or aromatic halides. Representative of some common organic solvents are alcohols such as methanol, ethanol, i-propanol, cyclohexanol, benzyl alcohol, 2-octanol, ethylene glycol, propylene glycol, and glycerol; aliphatic hydrocarbons such as pentane, cyclohexane, heptanes, VM&P solvent, and mineral spirits; alkyl halides such as ethyl chloride, and chlorobenzene; amines such as isopropylamine, cyclohexylamine, ethanolamine, and diethanolamine; aromatic hydrocarbons such as benzene, toluene, ethyl benzene, and xylene, esters such as ethyl acetate, isopropyl acetate, ethyl acetoacetate, amyl acetate, isobutyl isobutyrate, and benzyl acetate; ethers such ethyl ether, n-butyl ether, tetrahydrofuran, and 1,4-dioxane; glycol ethers such as ethylene glycol monomethyl ether, ethylene glycol monomethyl ether acetate, diethyleneglycol monobutyl ether, and propylene glycol monophenyl ether; ketones such as acetone, methyl ethyl ketone, cyclohexanone, diacetone alcohol, methyl amyl ketone, and diisobutyl ketone; petroleum hydrocarbons such as mineral oil, gasoline, naptha, kerosene, gas oil, heavy oil, and crude oil; lubricating oils such as spindle oil and turbine oil; and fatty oils such as corn oil, soybean oil, olive oil, rape seed oil, cotton seed oil, sardine oil, herring oil and whale oil.

Other miscellaneous organic solvents can also be used such as acetonitrile, nitromethane, dimethylforamide, propylene oxide, trioctyl phosphate, butyrolactone, furfural, pine oil, turpentine, and m-creosol.

It is also intended herein to encompass by the term "solvent", volatile flavoring agents such as oil of wintergreen; peppermint oil; spearmint oil; menthol; vanilla; cinnamon oil; clove oil; bay oil; anise oil; eucalyptus oil; thyme oil; cedar leaf oil, oil of nutmeg; oil of sage; cassia oil; cocoa; licorice; high fructose corn syrup, citrus oils such as lemon, orange, lime and grapefruit; fruit essences such as apple, pear, peach, grape, strawberry, raspberry, cherry, plum, pineapple, and apricot; and other useful flavoring agents including aldehydes and esters such as cinnamyl acetate, cinnamaldehyde, eugenyl formate, p-methylanisol, acetaldehyde, benzaldehyde, anisic aldehyde, citral, neral, devanal, vanillin, tolyl aldehyde, 2,6-dimethyloctanal, and 2-ethyl butyraldehyde. In addition, it is intended that the term solvent include volatile fragrances such as natural products and perfume oils. Some representative natural products and perfume oils are ambergris, benzoin, civet, clove, leaf oil jasmine, mate, mimosa, musk, myrrh, orris, sandalwood oil and vetivert oil; aroma chemicals such as amyl salicylate, amyl cinnamic aldehyde, benzyl acetate, citronellol, coumarin, geraniol, isobornyl acetate, ambrette, and terpinyl acetate; and the various classic family perfume oils such as the flora bouquet family, the oriental family, the chypre family, the woody family, the citrus family, the canoe family, the leather family, the spice family, and the herbal family.

In certain aspects, the compositions further comprise: at least one topical medicament. Suitable representative topical medicaments include, but are not limited to, antibiotics (including triple antibiotics).

In certain aspects, the compositions further comprise: at least one analgesic. Suitable representative analgesics include, but are not limited to, capsaicin, methyl salicylate, menthol, triethanolamine salicylate, or a mixture thereof.

In certain aspects, the compositions further comprise: at least one essential oil. Suitable representative essential oils include, but are not limited to, natural mosquito repellent oil, citronella oil, and combinations thereof.

In certain aspects, the compositions further comprise: at least one preservative. In certain aspects, the compositions further comprise: at least one colorant.

In certain aspects, the compositions further comprise: at least one fragrance.

In certain aspects, said siloxane copolymer is dimethicone crosspolymer

In certain aspects, said first solvent, said first additional solvent, and/or said second additional solvent are selected independently from methylsiloxane cyclics having 4 and 5 silicon atoms (such as cyclopentasiloxane), a trimethylsiloxy end-blocked polydimethylsiloxane, ester of aromatic alkoxylated alcohol and fatty carboxylic acid, alkoxylated derivatives of benzyl alcohol (such as PPG-3 benzyl ether ethyl hexanoate), and mixtures thereof.

In certain aspects, the compositions, comprise:
dimethicone crosspolymer;
cyclopentasiloxane;
PPG-3 benzyl ether ethyl hexanoate;
octadecyldimethyl trimethoxysilylpropyl ammonium chloride; and
benzalkonium chloride.

In certain aspects, the invention is directed to methods of employing the compositions described therein. In certain aspects, the composition is in the form of a gel. In certain aspects, said composition is in the form selected from the group consisting of: hand sanitizer, antiperspirant, deodorant, skin cream, skin care lotion, moisturizer, acne remover, wrinkle remover, facial cleanser, bath oil, perfume, cologne, sachet, sunscreen, pre-shave lotion, after-shave lotions, liquid soap, shaving soap, shaving lather, shaving gel, hair shampoo, hair conditioner, hair spray, mousse, permanent, depilatory, cuticle coat, make-up, color, cosmetic, foundation, blush, lipstick, lip balm, eyeliner, mascara, oil remover, cosmetic remover, delivery system for oil and water soluble substance, powder, and mixtures thereof.

The present invention is further defined in the following Examples, in which all parts and percentages are by weight and degrees are Celsius, unless otherwise stated. It should be understood that these examples, while indicating preferred aspects of the invention, are given by way of illustration only. From the above discussion and these examples, one skilled in the art can ascertain the essential characteristics of this invention, and without departing from the spirit and scope thereof, can make various changes and modifications of the invention to adapt it to various usages and conditions.

EXAMPLES

Example 1

Samples of the composition of this invention were prepared by blending components A or B with both C and D. All of the weights are in grams.

The samples were then tested. The test subjects were Caucasian females.

About 1.0 g of each composition was applied to the back of the hand of the test subject. All of the comments were obtained within 60 seconds after application and evaluation of each composition.

The compositions and comments from the test subjects are shown in Table I.

TABLE I

| Materials | Sample 1 | Sample 2 |
|---|---|---|
| A | 40 | |
| B | | 40 |
| C | 1.6 | 1.5 |
| D | 1.2 | 0.7 |
| Comments | Slick feel, oily feel | Grabby feel, wet feel |

A = Dow Corning 9040 elastomer blend (a mixture of high molecular weight silicone elastomers (dimethicone crosspolymer) in cyclopentasiloxane
B = Dow Corning 9045 elastomer blend (a mixture of high molecular weight silicone elastomers (dimethicone crosspolymer) in cyclopentasiloxane
C = a mixture of methylsiloxane cyclics having 4 and 5 silicon atoms, respectively
D = a trimethylsiloxy end-blocked polydimethylsiloxane having 100 cS viscosity Example 2

Samples were prepared as shown in Example 1. The compositions and comments from the test subjects are shown in Table II.

TABLE II

| Materials | Sample 1 | Sample 2 | Sample 3 | Sample 4 | Sample 5 | Sample 6 | Sample 7 |
|---|---|---|---|---|---|---|---|
| | Components (in grams) | | | | | | |
| A | 15 | 15 | 15 | 15 | 15 | 15 | 15 |
| C | 1.69 | | | | 0.55 | 0.2 | 3 |
| E | | 1 | | | | 1 | |

TABLE II-continued

|  | Sample 1 | Sample 2 | Sample 3 | Sample 4 | Sample 5 | Sample 6 | Sample 7 |
|---|---|---|---|---|---|---|---|
| D |  |  | 0.25 |  |  |  |  |
| F |  |  |  | 0.35 |  |  |  |
| G | 0.00015 | 0.00015 | 0.00015 | 0.00015 | 0.00015 | 0.00015 | 0.00015 |
| Tester | | | Ratings (1 = best feel; 10 = worst feel) | | | | |
| 1 | 5 |  | 10 |  | 1 |  |  |
| 2 |  |  |  | 1 | 1 |  |  |
| 3 | 5 | 5 | 1 | 1 | 1 | 10 | 10 |
| 4 | 3 | 5 | 3 | 1 | 1 | 3 | 10 |
| 5 | 1 |  |  |  |  |  | 10 |
| Comments | Slippery, wet feel | Balls up, does not spread | Balls up, does not spread | Slick feel, sticky feel | Slick feel, spreads | Oily | Very slippery, oily |

A = Dow Corning 9040 elastomer blend (a mixture of high molecular weight silicone elastomers (dimethicone crosspolymer) in cyclopentasiloxane
C = a mixture of methylsiloxane cyclics having 4 and 5 silicon atoms, respectively
D = a trimethylsiloxy end-blocked polydimethylsiloxane having 100 cS viscosity
E = a trimethylsiloxy end-blocked polydimethylsiloxane having 50 cS viscosity
F = a trimethylsitoxy end-blocked polydimethylsiloxane having 1000 cS viscosity
G = preservative Example 3

Samples were prepared as shown in Example 1. The compositions and comments from the test subjects are shown in Table III.

TABLE III

| Materials | Sample 1 | Sample 2 | Sample 3 | Sample 4 |
|---|---|---|---|---|
| A | 3000 | 94.047 | 94.047 | 94.047 |
| C | 111 |  |  |  |
| H |  | 5.416 | 5.416 | 5.416 |
| G | 0.5 | 0.0009 | 0.0009 | 0.0009 |
| I |  | 0.527 | 1.54 | 0.263 |
| Comments | Slick feel, spreads | Slick feel, spreads | Slick feel, spreads | Slick feel, spreads easily |

A = Dow Corning 9040 elastomer blend (a mixture of high molecular weight silicone elastomers (dimethicone crosspolymer) in cyclopentasiloxane
C = a mixture of methyl siloxane cyclics having 4 and 5 silicon atoms, respectively
G = preservative
H = Crodamol SFX ester of aromatic alkoxylated alcohol and fatty carboxylic acid
I = $(CH_3O)_3Si(CH_2)_3N^+$ dimethyloctadecyl chloride Example 4

This example tests the compositions of the invention (in the form of a gel) in killing or reducing E. coli that has be inoculated into the gel containing the compositions of the invention.
Method 1:
The formulations were prepared, one with the antimicrobial and one without the antimicrobial as a control. A saline solution with approximately 1000 CFU/ml E. coli was prepared and used as the inoculum. The formulation was placed in resealable plastic bags and 3 ml of the inoculum added to each. Also, a separate bag with 3 ml of only inoculum was used as a positive control.

The E. coli used, purchased from Quanti-Cult™, was derived from original ATCC stock cultures. They were received dehydrated. They are then rehydrated, and transferred to a sterile Erlenmeyer flask containing 100 ml of tryptic soy broth and incubated overnight at 35° C. The cultures were only used for testing on that day. A 1 ml aliquot of that culture was put into a clean flask with fresh broth daily.

The formulations were exposed for 60 minutes. Since the formulation is very hydrophobic, the bags were kneaded every 10 minutes to ensure contact of the inoculum with the material. At the end of the exposure period, 5 grams of material was placed in petri dishes (in triplicate), spread with a sterile cotton swab and then covered with tryptic soy agar and incubated for 24 hours at 35° C. At the end of the incubation period colony counts were compared. The results are shown below.
Method 2:
The compositions were prepared as above and the same method used. However, five exposure periods were investigated (60 seconds, 60 minutes, 4 hours, 8 hours and 24 hours). Also, at the end of the exposure periods, rather than spreading the composition in petri dishes, only the inoculum that separated from the gel in the releasable plastic bag was incubated and tested for bacteria. Equal volumes of the inoculum was withdrawn carefully from each of the bags and covered with tryptic soy agar as above, incubated for 24 hours at 35'C and colony counts compared at the end of the incubation period.

When an appropriate exposure period was determined, the experiment was repeated using various levels of bacteria.

Control samples were also evaluated. This included gel without any antimicrobial agent (designated as "Comparative") and a control utilizing only the releasable plastic bag (designated as "Control").
Study 1 Exposure Time This study evaluated the length of time for the effectiveness of the gel of the invention to eliminate or reduce the amount of bacteria. A 3-8 ml incubated 3000 CFU/ml E. coli sample was introduced into a releasable plastic bag containing the gel of the invention for increasing times of exposure. The times of exposure were:
  60 seconds
  60 minutes
  4 hours
  8 hours
  24 hours
After which the sample of E. coli were incubated and the colony count were performed. Each sample was run in triplicate for a total of 18 samples Study 2 Concentration Study This study evaluated the effectiveness of gel of the invention to eliminate or reduce the amount of increasing amounts of bacteria. A 3-8 ml *E. coli* sample containing increasing amounts of *E. coli* was introduced into a releasable plastic bag containing gel of the invention. The colony counts were:

0 CFU/ml
1000 CFU/ml
3000 CFU/ml
6000 CFU/ml

Each sample was exposed to the gel of the invention for a specific time based on the effectiveness in Study 1. After which the sample of *E. coli* was incubated and the colony count was performed. Each sample was run in triplicate for a total of 12 samples.

| Sample | Results |
|---|---|
| Inoculums alone in releasable plastic bag (control) | Too numerous to count |
| Gel (with antimicrobial) | Average 40 CFU/plate |
| Gel (without antimicrobial) (comparative) | Average 91 CFU/plate |

Example 5

The routine use of lotions to minimize the development of dermatitis on hands of health professionals that undergo many wash procedures per day has been a component of infection control recommendations for many years. In the past, the primary role for these lotions was to lubricate epithelial tissue and replace emollients that were removed. The purpose of this example was to examine antimicrobial properties of a hand sanitizer of the invention (containing dimethicone crosspolymer; cyclopentasiloxane; PPG-3 benzyl ether ethyl hexanoate, octadecyldimethyl trimethoxysilylpropyl ammonium chloride; and benzalkonium chloride) using the gram-negative *bacillus Serratia marcescens* as an indicator microorganism for effectiveness.

Experiments were developed to initially determine the antimicrobial activity following bacterial challenge on hands coated with the hand gel. The product was also tested for extended effectiveness during prolonged glove use by volunteers. Finally, the ability of hand sanitizer to exhibit a demonstrable antibacterial effect following repeated hand washing was investigated.

Experimental Design

Phase 1:

Hands of potential volunteers for the investigation were initially screened for any observable skin conditions or injuries (i.e., broken skin) that could prevent them from participation in the project. The condition of the volunteers' hands was also visually evaluated throughout the three phases of the study. Four (4) volunteers were then instructed to wash their hands with a non-antimicrobial liquid soap and water for one minute to initially cleanse the skin before application of the experimental gel. A small amount (dime size) of hand sanitizer was then applied onto the participants' hands and rubbed vigorously into the skin. Immediately after this application, a 2×2" square section of the dorsal surface of each hand was swabbed with a 1:100,000 dilution (left hand) and a 1:1,000,000 dilution (right hand) of a 24-hour broth culture of the red-pigmented bacterial species, *S. marcescens*. These two bacterial dilutions were used following multiple preliminary experiments that were carried out to determine concentrations of *S. marscecens* that would reproducibly challenge hand gel activity. The resultant concentrations of *S. marscecens* used to challenge hands were approximately $1 \times 10^5$ bacteria/mL (left hand) and $1 \times 10^4$ bacteria/mL (right hand), respectively. Applied bacterial suspensions were allowed to dry before proceeding with further testing. Subsequently, antibacterial activity of hand sanitizer as determined by the presence of *S. marcescens* at the application sites was assayed by swabbing the 2×2" test areas with sterile cotton swabs moistened in sterile trypticase soy broth. Sample intervals of 1 minute, 30 minutes, 2, 4, 6, and 8 hours were utilized. Collected samples were streaked onto trypicase soy agar plates and incubated aerobically at room temperature for 48-72 hours. Incubation of *S. marcescens* under these conditions allowed for both microbial growth and red pigment production by the bacteria.

Phase 2:

Four volunteers initially prepared their hands as described above. Hand sanitizer was applied to both hands and allowed it to dry, followed by application of the 1:100,000 and 1:1,000,000 dilutions of cultured *S. marcescens*. Hands were allowed to dry and zero minute control samples were taken before proceeding. Participants then washed their hands for 15 seconds with a non-antimicrobial soap after sampling at designated periods of 0 (control) minutes, 30 minutes, 2, 4, 6 and 8 hours. Samples were taken from the *S. marcescens*-seeded hand sites using sterile broth moistened cotton swabs, cultured on trypticase soy agar plates, incubated, and observed for bacterial growth as described above.

Phase 3:

The participants washed their hands as described above prior to the glove use portion of the investigation, followed by application of hand sanitizer. The *S. marcescens* test dilutions were swabbed onto the right and left hand test sites, respectively. Participants then donned nitrile gloves and continued to wear them for one hour while performing routine work tasks. At the end of this interval gloves were removed, samples collected from test sites using moistened cotton swabs, and trypticase soy agar plates seeded with material from the skin. Prepared culture plates were incubated at room temperature for 48-72 hours prior to observation for red-pigmented *S. marcescens* colonies.

Results:

Phase 1:

Sixteen (16) test samples from each *S. marcescens* dilution (1:100,000 and 1:1,000,000) were assayed. Culture findings are presented in Table 1. All *S. marcescens* control cultures collected without exposure to the hand gel yielded confluent bacterial growth. With regard to the 1-minute samples, 25/32 cultures were positive for red-pigmented colonies. These showed higher levels of bacterial growth on each plate than was detected for later experimental collection intervals. In most cases the pigmented growth for the one minute-exposure plates was similar in intensity per plate to that noted for the positive control plates, or was slightly less. For all other test cultures where positive growth was observed, the presence of bacteria cultured for these intervals was considerably less. It was interesting to note that as the time intervals of skin exposure to hand sanitizer increased, the resultant detection of *S. marcescens* colonies decreased, until by six hours none of the test cultures yielded red-pigmented colonies (0/32). No hand dermatitis problems were noted for any of the volunteers.

TABLE 1

Effect of Hand Sanitizer with Repeated Bacterial Exposure

| Sample Time | 1:100,000 dilution | 1:1,000,000 dilution |
| --- | --- | --- |
| Control plates | 18/18 | 18/18 |
| 0 minutes | 17/18 | 5/18 |
| 30 minutes | 3/18 | 0/18 |
| 2 hours | 1/18 | 0/18 |
| 4 hours | 0/18 | 0/18 |
| 6 hours | 0/18 | 0/18 |
| 8 hours | 0/18 | 0/18 |

Phase 2:

Eighteen (18) test samples of each dilution were completed for Phase 2 and the observed results are presented in Table 2. The zero-minute time interval represented the only sampling before any hand washing had occurred. The observed results were comparable to the one-minute data obtained in Phase 1, in that all test samples produced positive results but the per plate quantity of growth was much less than that observed on the corresponding positive controls. All other positive test cultures observed at later time intervals produced considerably less pigmented growth, much like what was seen for cultures in Phase 1. No hand dermatitis problems were noted for any of the volunteers.

TABLE 2

Effect of Hand Gel with Repeated Handwashing and Bacterial Exposure

| Sample Time | 1:100,000 dilution | 1:1,000,000 dilution |
| --- | --- | --- |
| Control plates | 18/18 | 18/18 |
| 0 minutes | 17/18 | 5/18 |
| 30 minutes | 3/18 | 0/18 |
| 2 hours | 1/18 | 0/18 |
| 4 hours | 0/18 | 0/18 |
| 6 hours | 0/18 | 0/18 |
| 8 hours | 0/18 | 0/18 |

Phase 3:

All except one (15/16) experimental cultures from samples taken after removal of gloves were negative for red-pigmented bacteria (Table 3). In contrast, in a separate positive control assay, a participant applied bacteria only and wore gloves for one hour without the use of hand sanitizer. Resultant cultures from control test sites were positive (4/4). The qualitative presence of *S. marcescens* in these controls was much less than that found for control plates using diluted bacteria only (16/16). No hand dermatitis problems were noted for any of the volunteers.

TABLE 3

Effect of Hand Gel during Glove Use

| Sample Time | 1:100,000 dilution | 1:1,000,000 dilution |
| --- | --- | --- |
| Control plates | 16/16 | 16/16 |
| 1 hour | 1/16 | 0/16 |

SUMMARY

The example demonstrated that the hand sanitizer of the invention provided an antimicrobial benefit. Laboratory testing with *S. marcescens* demonstrated that the gel was effective in inhibiting test bacteria applied onto the skin during multiple hand wash procedures and prolonged wearing of gloves. Additionally, none of the participating volunteers demonstrated any irritation dermatitis symptoms with exposure to the hand sanitizer.

When ranges are used herein for physical properties, such as molecular weight, or chemical properties, such as chemical formulae, all combinations, and subcombinations of ranges specific aspects therein are intended to be included.

The disclosures of each patent, patent application and publication cited or described in this document are hereby incorporated herein by reference, in its entirety.

Those skilled in the art will appreciate that numerous changes and modifications can be made to the preferred aspects of the invention and that such changes and modifications can be made without departing from the spirit of the invention. It is, therefore, intended that the appended claims cover all such equivalent variations as fall within the true spirit and scope of the invention.

What is claimed is:

1. A hand sanitizer composition, consisting of benzalkonium chloride, dimethicone crosspolymer, cyclopentasiloxane, and PPG-3 benzyl ether ethyl hexanoate.

2. A method of disinfecting a skin surface, comprising applying to the skin a hand sanitizer composition according to claim 1.

* * * * *